US009259563B2

(12) United States Patent
Klingel, Jr. et al.

(10) Patent No.: US 9,259,563 B2
(45) Date of Patent: Feb. 16, 2016

(54) FLUID TRANSFER ASSEMBLIES AND RELATED METHODS (75) Inventors: Robert R. Klingel, Jr., North Redington Beach, FL (US); Gerald L. Stadt, St. Petersburg, FL (US)

(73) Assignee: SAINT-GOBAIN PERFORMANCE PLASTICS CORPORATION, Aurora, OH (US)

( * ) Notice: Subject to any disclaimer, the term of this patent is extended or adjusted under 35 U.S.C. 154(b) by 674 days.

(21) Appl. No.: 12/406,590

(22) Filed: Mar. 18, 2009

(65) Prior Publication Data

US 2009/0243284 A1 Oct. 1, 2009

Related U.S. Application Data (60) Provisional application No. 61/037,490, filed on Mar. 18, 2008.

(51) Int. Cl.
*F16L 47/20* (2006.01)
*A61M 39/10* (2006.01)
*A61M 39/08* (2006.01)
*B29C 45/14* (2006.01)
*F16L 47/32* (2006.01)

(52) U.S. Cl.
CPC ............... *A61M 39/10* (2013.01); *A61M 39/08* (2013.01); *B29C 45/14614* (2013.01); *F16L 47/20* (2013.01); *F16L 47/32* (2013.01); *A61M 2205/6081* (2013.01); *Y10T 403/66* (2015.01)

(58) Field of Classification Search
USPC ........ 285/125.1, 130.1, 133.11, 133.5, 148.7, 285/285.1, 286.1, 293.1, 294.1, 294.2, 285/381.4, 369, 417; 264/261, 263
See application file for complete search history.

(56) References Cited

U.S. PATENT DOCUMENTS

| 1,365,025 | A | * | 1/1921 | Elder | 285/32 |
| 2,009,068 | A | * | 7/1935 | Porter et al. | 285/285.1 |
| 2,706,134 | A | * | 4/1955 | Wilson et al. | 239/204 |
| 2,739,829 | A | * | 3/1956 | Cundiff et al. | 285/21.2 |
| 3,826,521 | A | * | 7/1974 | Wilhelmsen | 285/15 |
| 4,070,044 | A | * | 1/1978 | Carrow | 285/133.11 |

(Continued)

FOREIGN PATENT DOCUMENTS

CN 2350964 Y 12/1999
CN 2557784 Y 6/2003

(Continued)

OTHER PUBLICATIONS

International Search Report and Written Opinion dated Sep. 24, 2009 issued in PCT Application No. PCT/ US2009/001519, 10 pages.

(Continued)

*Primary Examiner* — Aaron Dunwoody
*Assistant Examiner* — Fannie Kee
(74) *Attorney, Agent, or Firm* — Abel Law Group, LLP; Chi Suk Kim (57) ABSTRACT An assembly includes a first polymeric connector having a first passageway and a second passageway fixed relative to the first passageway; a first polymeric conduit having a third passageway in fluid communication with the first passageway; and a polymeric member extending over a gap between the first connector and the first conduit and at least portions of outer surfaces of the first connector and the first conduit. The first passageway is in fluid communication with the third passageway.

20 Claims, 8 Drawing Sheets

(56) References Cited

U.S. PATENT DOCUMENTS

| | | | |
|---|---|---|---|
| 4,396,046 A | 8/1983 | Kentosh | |
| 4,420,176 A * | 12/1983 | Cornwall | 285/142.1 |
| H0000176 H * | 12/1986 | Johnstone, Jr. | 285/31 |
| 4,662,655 A * | 5/1987 | Fliervoet et al. | 285/24 |
| 4,783,099 A * | 11/1988 | Muser | 285/7 |
| 5,248,172 A | 9/1993 | Wilson | |
| 5,356,587 A | 10/1994 | Mitsui et al. | |
| 6,270,125 B1 * | 8/2001 | Rowley et al. | 285/242 |
| 6,290,265 B1 | 9/2001 | Warburton-Pitt et al. | |
| 7,093,859 B2 | 8/2006 | Warburton-Pitt et al. | |
| 7,407,612 B2 | 8/2008 | Warburton-Pitt et al. | |
| 7,708,923 B1 | 5/2010 | Helicke et al. | |
| 2002/0033599 A1 * | 3/2002 | Robertson | 285/31 |
| 2003/0093107 A1 | 5/2003 | Parsonage et al. | |
| 2003/0233074 A1 | 12/2003 | Shields | |
| 2005/0043712 A1 | 2/2005 | Devens, Jr. | |
| 2005/0131357 A1 | 6/2005 | Denton et al. | |

FOREIGN PATENT DOCUMENTS

| | | |
|---|---|---|
| JP | 1992-008535 A | 1/1992 |
| JP | 1992-290712 A | 10/1992 |
| JP | 1992-321894 A | 11/1992 |
| JP | 1993-096646 A | 4/1993 |
| JP | 2547428 B | 10/1996 |
| JP | 2547428 B2 | 10/1996 |
| JP | 1997-229284 A | 9/1997 |
| JP | 9-323357 | 12/1997 |
| JP | 1999-006595 A | 1/1999 |
| JP | 2003-042378 A | 2/2003 |
| JP | 2004-100767 A | 4/2004 |
| WO | 2007038841 A1 | 4/2007 |

OTHER PUBLICATIONS

Procedure for Short Term Burst Testing and Static Testing Using the Hydraulic Testing Equipment, Saint-Gobain Performance Plastics—Akron, Apr. 3, 1998, 8 pages, Revision No. 1.

* cited by examiner

FLUID TRANSFER ASSEMBLIES AND RELATED METHODS

RELATED APPLICATION

This application claims the benefit of U.S. Provisional Patent Application Ser. No. 61/037,490, filed Mar. 18, 2008, the contents of which are hereby incorporated by reference herein.

TECHNICAL FIELD

The invention relates to fluid transfer assemblies, related methods, and methods for transferring fluids.

BACKGROUND

Flexible polymer tubing can be used as conduits or flow paths to transfer fluid from a source to a desired destination. In some cases, as the fluid is transferred from the source to the destination, other material is added to the fluid. The fluid, with or without added material(s), can also be transferred (e.g., diverted) to multiple destinations such that the destinations have different compositions. As an example, in pharmaceutical manufacturing, a drug from a source can be transferred to a first destination through a flexible tubing. As the drug travels along the tubing, other ingredient(s) can be delivered through other fluidly-connected tubing to combine with the drug, and the resulting combination can be delivered to the first destination. The drug (with or without other ingredient(s)) can be delivered to other destinations by controlling the flow paths of the drug and the ingredient(s). The compositions in these other destinations may be different from or the same as the composition in the first destination.

SUMMARY

Embodiments may include one or more of the following features.

In one aspect, the invention features fluid transfer assemblies, related methods, and methods for transferring fluids (such those used in the medical industry or pharmaceutical industry). The assemblies and methods include a first connector attached to a conduit or a second connector by a polymeric member. The attached first connector and conduit or second connector are capable of providing a fluid transfer assembly that can be easily tailored and that has strong, fluid-tight connections.

In another aspect, the invention features a method of attaching a first polymeric connector having a first passageway and a second passageway fixed relative to the first passageway, and a first polymeric conduit having a third passageway, the method comprising attaching the first polymeric connector to the first polymeric conduit with a first polymeric member extending over at least portions of outer surfaces of the first connector and the first conduit, the first passageway being in fluid communication with the third passageway.

In another aspect, an assembly is provided, the assembly comprising a first polymeric connector having a first passageway and a second passageway fixed relative to the first passageway, a first polymeric conduit having a third passageway in fluid communication with the first passageway, and a polymeric member extending over a gap between the first connector and the first conduit and at least portions of outer surfaces of the first connector and the first conduit.

In another aspect, the invention features a method including flowing a fluid from a first location to a second location through a fluid transfer assembly described herein.

Other aspects, features and advantages will be apparent from the description of the embodiments thereof and from the claims.

DETAILED DESCRIPTION

Figure 1:
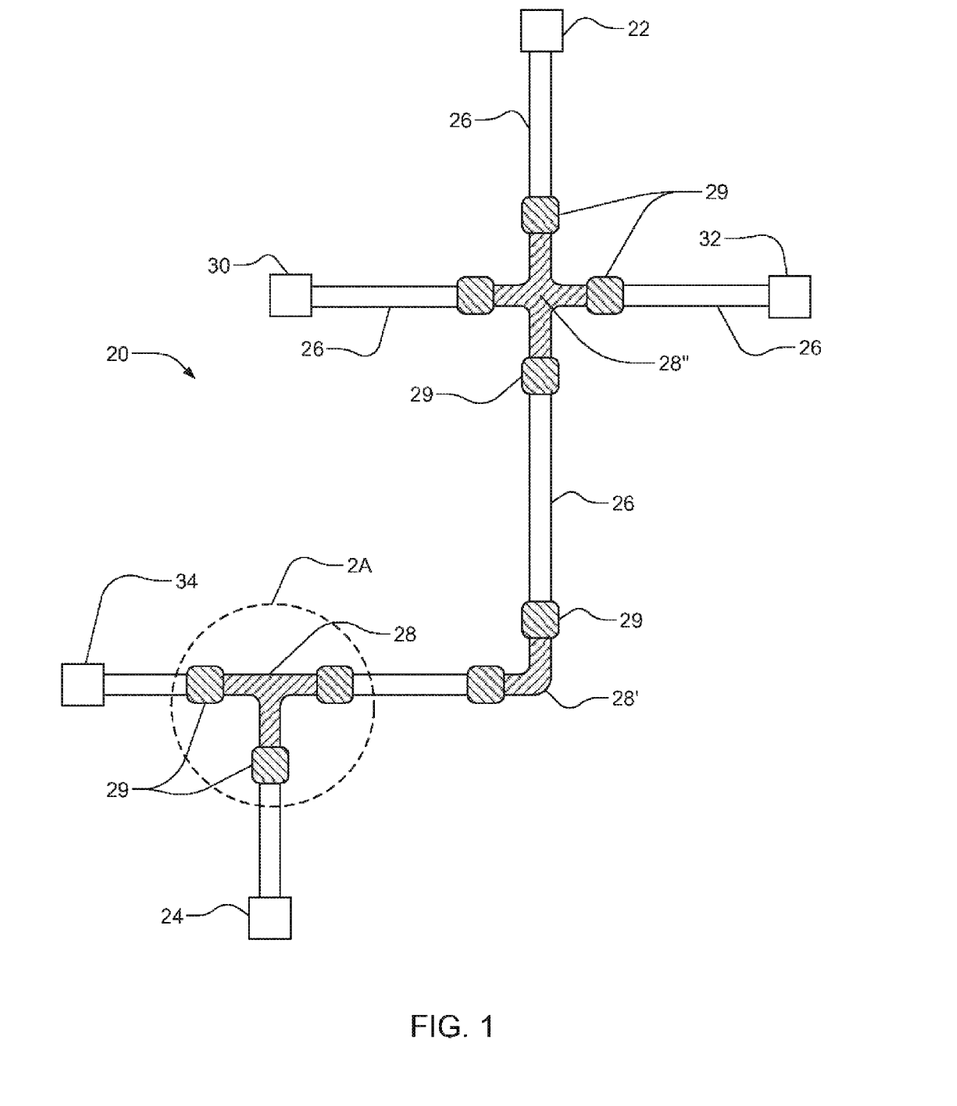
FIG. 1 is a schematic diagram of a fluid transfer assembly.

FIG. 1 shows a fluid transfer assembly 20 in which a fluid (e.g., a drug in a carrier) from a source 22 is transferred to a destination 24 through a series of conduits 26 (such as flexible polymeric tubing) and connectors 28, 28', 28". Connectors 28, 28', 28" and conduits 26 are attached in fluid communication with each other by polymeric members 29 that, as shown, are in the shape of cylindrical collars. As the fluid travels through assembly 20, additional materials from sources 30, 32, 34 are added through other conduits 26 and connectors 28, 28', 28" to provide a desired final composition at destination 24. Referring also to FIGS. 2A, 2B, 3, 4 and 5, connectors 28, 28', 28" can have a variety of configurations including: a T-shaped configuration 28 having three ends (FIGS. 2A and 2B), a Y-shaped configuration 28''' having three ends (FIG. 3), an L-shaped configuration 28' having two ends (FIG. 4), and a cross-shaped configuration 28" (FIG. 5) having four ends. The various configurations of connectors allow fluid transfer assembly 20 to be tailored, for example, to fit within a desired space and/or to yield the desired final composition at destination 24. Numerous configurations of fluid transfer assemblies can be formed by varying the number, type and location of connectors, conduits and material sources. For example, while assembly 20 includes only one destination 24, in other embodiments, the assembly includes multiple destinations that include different compositions and/or share the same composition.

Figure 2A:
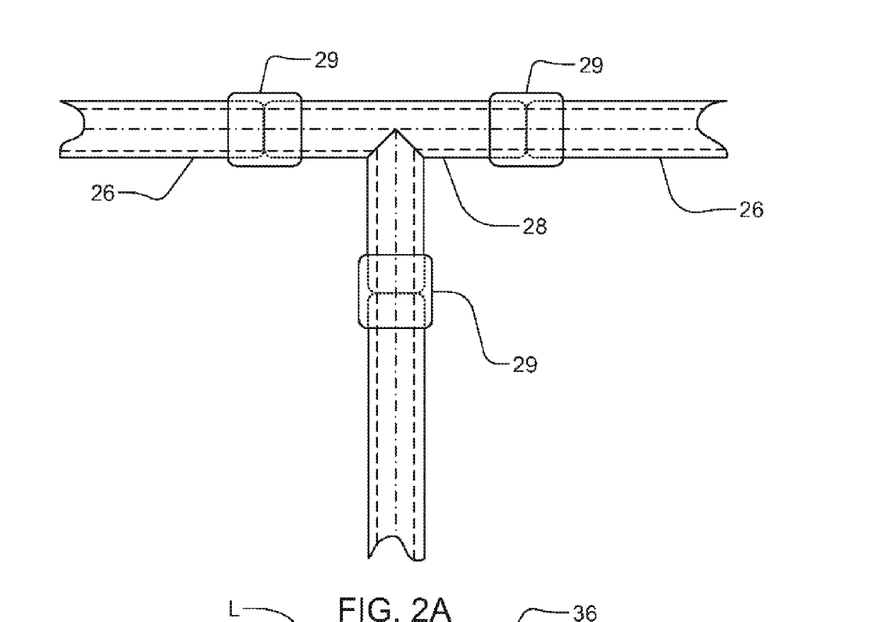
FIG. 2A is a detailed view of area 2A in FIG. 1.
Figure 2B:
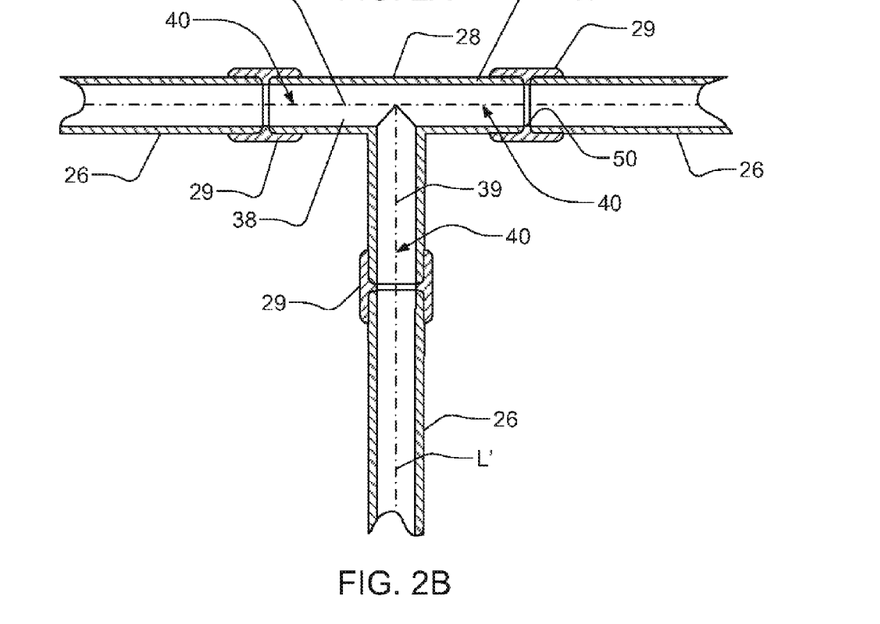
FIG. 2B is a cross-sectional view of FIG. 2A.

Referring particularly to FIG. 2B, connectors (as shown, T-shaped connector 28) are pre-formed polymeric pieces configured to place two or more passageways in fluid communication with each other. A passageway can be defined by a conduit or another connector. A connector includes a polymeric body 36 that defines a first passageway 38 having a long axis L and at least one other passageway 39 transversely fixed relative to the first passageway and having a long axis L'. As used herein, a passageway is a volume defined by portions whose long axes are substantially collinear. For example, T-shaped connector 28 includes two passageways 38, 39 that are fixed orthogonally relative to each other; L-shaped or elbow-shaped connector 28' includes at least two passageways, depending on the radius of curvature of the bend in the connector; cross-shaped connector 28" includes two passageways that are fixed orthogonally relative to each other; and Y-shaped connector 28''' includes three passageways that are fixed relative to each other. In comparison, a flexible polymeric tube can have multiple passageways (e.g., when different portions of the tube are bent), but the passageways are not fixed relative to each other without a means of holding the portions in place. Along its long axis, the diameter or average width of a passageway can be substantially constant or different. The passageways can have a circular cross section or a non-circular cross section (e.g., oval, elliptical, irregularly or regularly polygonal, symmetrical, asymmetrical).

A connector further includes two or more end openings configured to be placed in fluid communication with an opening of a conduit or another connector. For example, T-shaped connector 28 includes three end openings 40; L-shaped connector 28' includes two end openings 40; cross-shaped connector 28" includes four end openings 40; and Y-shaped connector 28''' includes three openings. A connector may also be used to join two conduits axially together, end-to-end. The end openings, like the passageways, can have a circular cross section or a non-circular cross section (e.g., oval, elliptical, irregularly or regularly polygonal, symmetrical, asymmetrical). The diameter or average width of the end openings can be the same as or different from the diameter or average width of the passageway of a connector and/or a conduit attached to the connector. The assembly may be designed with no portion having an inner diameter that is less than that of the conduits used. Connectors can be formed, for example, by injection molding or cast molding.

Conduits 26 can be any flexible body having a passageway that can be used to transport the desired fluid(s). An example of a conduit is an extruded flexible polymer tube having two end openings and one unfixed passageway between the openings. The size of conduit, such as its length and cross section, is not limited. Conduit 26 can include a single material or multiple materials (e.g., arranged in layers), as described in U.S. Patent Publication No. 2005/0043712. Conduit 26 can have a circular cross section or a non-circular cross section (e.g., oval, elliptical, irregularly or regularly polygonal, symmetrical, asymmetrical).

Figure 2C:
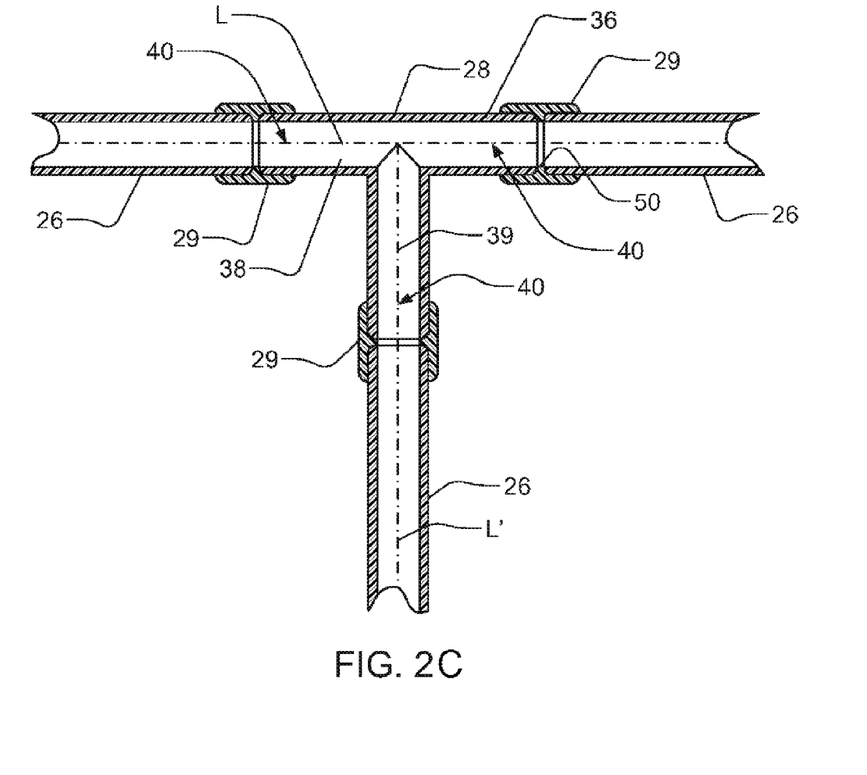
FIG. 2C is a cross-sectional view of FIG. 2A.
Figure 3:
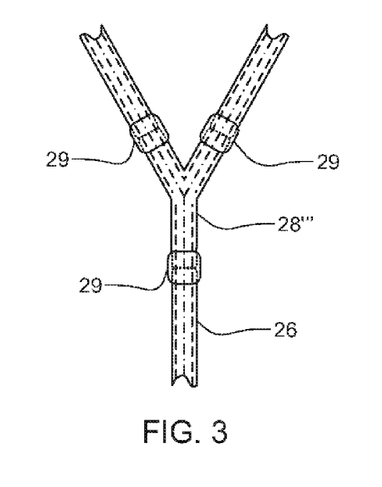
FIG. 3 is a side view of an embodiment of a connector connected to tubing.
Figure 4:
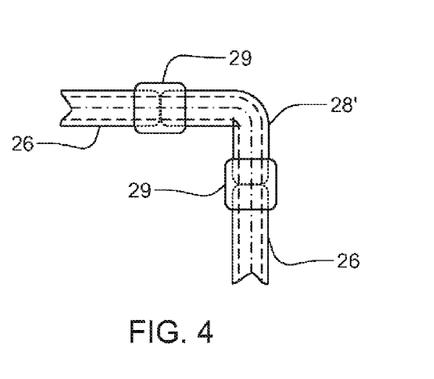
FIG. 4 is a side view of an embodiment of a connector connected to tubing.
Figure 5:
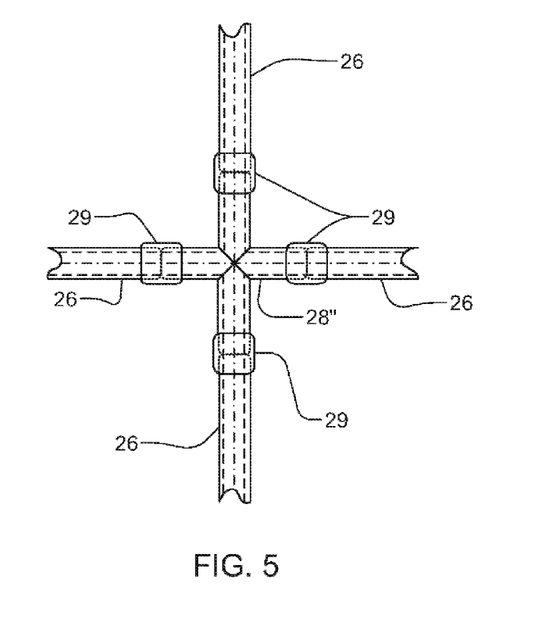
FIG. 5 is a side view of an embodiment of a connector connected to tubing.

Connectors 28, 28', 28", 28''', conduits 26 and polymeric members 29 (described below) can include (e.g., be formed of) a polymer or a combination of different polymers (e.g., copolymers, alloys, blends) used to transport the desired fluid(s), e.g., without adverse or unwanted reaction with the fluid(s). The compositions of connectors 28, 28', 28", 28''', conduits 26 and polymeric members 29 can be the same or different. In some embodiments, the compositions are selected based on their bonding properties so as to provide a strong, fluid-tight attachment. Examples of polymers include thermoplastics, thermosets, elastomers, thermoplastic elastomers, and engineering thermoplastic elastomers. As can be seen in FIG. 2C, for example, one or more embodiments of the present invention may include a polymeric connector, a polymeric conduit, and a polymeric member constructed of one or more thermoplastic elastomers. Specific examples of polymers include polyureas, polyvinyls, polyvinyl chlorides (e.g., Tygon®), polypropylene, high density polyethylene, polyacrylics, copolymers and block copolymers thereof, such as block copolymers of polyether and polyamide, e.g., Pebax®, GRILON®, GRILAMID® (EMS), VESTAMID® (Creanova), C-Flex® thermoplastic elastomer (Consolidated Polymer Technologies, Inc.), ethylene propylene diene monomer (EPDM), epichlorohydrin, nitrile butadiene elastomers, epoxies, isocyanates, polycaprolactone, poly(dimethylsiloxane) containing polyurethanes and ureas, polysiloxanes, polybutylene terephthalate-polyethene glycol block copolymers (e.g., HYTREL®), polyurethanes, copolymers such as ABS (acrylonitrile-butadiene-styrene), styrene-butylene-styrene, styrene-ethylene-butylene-styrene compounds having Shore A hardness of from approximately 5 to approximately 95, ABS/nylon, ABS/-polyvinyl chloride (PVC), ABS/polycarbonate, acrylonitrile copolymer, polyacrylamide, polyacrylate and polyacrylsulfone, polyesters such as polyethylene terephthalate (PET), polybutylene terephthalate (PBT), polyethylene naphthalate (PEN), liquid crystal polymer (LCP), polyester/polycaprolactone and polyester/polyadipate, polyethers including polyetheretherketone (PEEK), polyethersulfone (PES), polyetherimide (PEI), polyetherketone (PEK), polymethylpentene, polyphenylene ether, polyphenylene sulfide, styrene acrylonitrile (SAN), polyamides such as nylons, ethylene, propylene ethylene vinylacetate and ethylene vinyl alcohol (EVA), various ionomers, polyethylene type I-IV, polyolefins, polyurethane, polyvinyl chloride, and polysiloxanes (silicones), fluoropolymers such as polychlorotriethylene (CTFE), poly[ethylene-co-chlorotrifluoroethylene] (ECTFE) copolymer ethylene tetrafluoroethylene (ETFE), copolymer tetrafluoroethylene and hexafluoropropylene (FEP), perfluoroalkane (PFA) and poly[vinylidene fluoride] (PVDF), and mixtures thereof. Examples of nylons include aliphatic nylons (such as Nylon 11 (Elf Atochem), Nylon 6 (Allied Signal), Nylon 6/10 (BASF), Nylon 6/12 (Ashley Polymers) Nylon 12 and aromatic nylons (such as GRIVORY® (EMS)) and Nylon MXD-6. Other nylons and/or combinations of nylons can be used.

Connectors and/or conduits may include identification markings or other indicia that may be printed or stamped onto the component. Tags such as bar code tags or RFID tags may also be included.

In some embodiments, connectors 28, 28', 28", 28''', conduits 26 and/or polymeric members 29 further include one or more additives incorporated into the polymer(s). For example, one or more polymers can include one or more additives (such as nano-materials (e.g., nano-tubes, nano-clays, fibers) and liquid crystalline polymers) capable of enhancing the strength of the polymer(s). Other examples of additives include coupling or compatibilizing agents, radio-opacifiers (e.g., bismuth oxychloride or barium sulfate), dispersants, stabilizers, plasticizers, surfactants, and/or pigments. Examples of additives are described in U.S. Patent Application Publication Nos. 2003/0093107 and 2005/0043712.

Still referring to FIG. 2B, fluid transfer assembly 20 can be formed by attaching the connectors (as shown, connector 28) to conduits 26 using polymeric members 29 to provide a fluid-tight seal. In some embodiments, pre-formed connector 28 and conduit 26 are placed and aligned in an appropriately figured cavity suitable for injection molding. The end openings of connector 28 and conduit 26 can have the same cross-sectional configuration and size such that, when they are coaxially aligned, they provide a smooth and substantially seamless transition (see below). The entire inner surfaces of connector 28 and conduit 26, or only portions thereof, may be flush. In some embodiments, connector 28 and conduit 26 have the same inner width/diameter but different outer widths/diameters. In other embodiments, connector 28 and conduit 26 have different cross-sectional configurations and different inner and outer widths/diameters. An end of connector 28 and an end of conduit 26 can be placed adjacent each other but not in contact so as to define a gap 50.

Polymeric member 29 can then be overmolded onto connector 28 and conduit 26 to form the assembly. More specifically, fluid material (prepolymer) for polymeric member 29 is then injected into the cavity such that the fluid material flows into gap 50, extends over outer end portions of connector 28 and conduit 26, and thermally bonds with the connector and the conduit. Having gap 50 and allowing polymeric member 29 to extend into the gap provides increased surface area (e.g., relative to having no gap) for bonding with the end walls of connector 28 and conduit 26, and a strong attachment among the connector, the conduit and the polymeric member. In some embodiments, polymeric member 29 does not extend into the passageways of connector 28 or conduit 26 such that there is a substantially smooth, seamless transition between the connector and the conduit. Having a substantially seamless transition between connector 28 and conduit 26 (e.g., without a protrusion extending radially inward from gap 50 into passageway 38, or a recess extending into the gap) prevents material from accumulating in fluid transfer assembly 20. In some embodiments, the protrusion or recess is less than approximately one mm. A seamless transition means that there is an absence of, or very few, visible craters, creases or seams at the transition and that the union is continuous and complete. As an example, to attach a ⅜ in inner diameter (I.D.)×¼ in outer diameter (O.D.) connector made of C-Flex® to a ⅛ in I.D.×¼ in O.D. flexible tubing made of C-Flex®, the gap between the ends of the connector and the tubing is approximately 3 mm, and the polymeric member extends approximately 3 mm from the ends of the connector and the tubing for a total collar length of about 9 mm. The above injection molded process can be repeated to form the desired fluid transfer assembly.

Connectors may also include inserts such as rods or pins that may be placed within the lumen of the connector and/or conduit when polymeric member 29 is to be molded. The insert may be removed from the assembly after the molding has been completed. An insert can limit the flow of liquid polymer so that it does not extend inside the inner diameter of the connector and/or conduit. Thus, a rod that has a diameter similar to the I.D. of the conduit and connector can help to form a smooth inner wall of constant diameter when a gap between the conduit and connector is filled. This smooth, constant diameter transition can result in better flow, more predictable mixing, and easier cleaning and disinfection. Constant I.D. conduits and connectors can also facilitate easier and more accurate calculations of fluid flow patterns throughout the system.

After the fluid material for polymeric member 29 solidifies, the assembly of connector, conduit and polymeric member is capable of having a tensile strength and/or burst strength substantially equal (e.g., within approximately 10%) to that of the conduit itself.

The polymeric members in a specific assembly can be molded individually in a sequential process or can be molded together in a single step. For example, referring to FIG. 2B, polymeric members 29 can be molded one at a time or simultaneously.

In the first instance, a mold can be designed to receive one branch of connector 28 (passageway 38) and one end of conduit 26. Each component is axially aligned and spaced properly to provide a desired gap between the ends. An insert may be used to align the components and/or to limit intrusion of prepolymer into the gap. Polymeric member 29 is then overmolded in place. The mold is removed, connector 28 is rotated, and the process is repeated with a second branch (passageway 39) and a second conduit 26. Finally, the process can be repeated with the third branch of the T. The same mold may be used for each polymeric member.

In the second instance, two or more connectors in a single assembly can be molded simultaneously using a single mold. For instance, if the T of FIG. 2B is to be overmolded, connector 28 can be placed in a mold and each of the three conduits 26 can then be aligned with the corresponding passages on the connector. Appropriate inserts may be used. The mold can be designed so that a single injection can provide prepolymer to each of the three polymeric members 29 that are to be overmolded. Thus, in a single step, each of the three polymeric members can be molded, providing for an increased rate of production. Molds may be designed to match the geometry of a specific assembly. Molds may also include inserts that can be optionally used to block flow of prepolymer to a specific site. Therefore, a single mold can be used to produce two different assemblies such as the assembly of FIG. 2B and the assembly of FIG. 5. The cross-shaped assembly of FIG. 5 can be produced in a mold that injects prepolymer to each of the four connection sites. The same mold can be used to produce the T assembly of FIG. 2B by using an insert or other blocking device to prevent the flow of prepolymer to the fourth site that is not present in the T assembly.

While a number of embodiments have been described, the invention is not so limited.

Figure 6A:
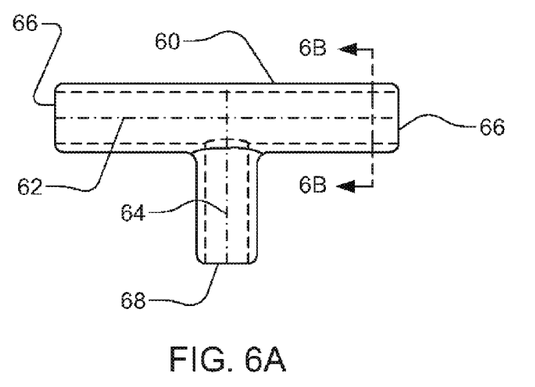
FIG. 6A is a side view of an embodiment of a connector.
Figure 6B:
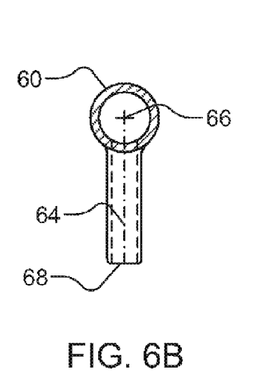
FIG. 6B is an end view of the connector shown in FIG. 6A, taken along line 6B-6B.

For example, FIGS. 6A and 6B show a T-shaped connector 60 having two passageways 62, 64 of different sizes, and end openings 66, 68 of different sizes. The different sizes allow differently-sized conduits and/or connectors to be attached to connector 60, and can provide different flow rates through connector 60. In other embodiments, a connector can have more than two differently-sized passageways and/or end openings.

Figure 7A:
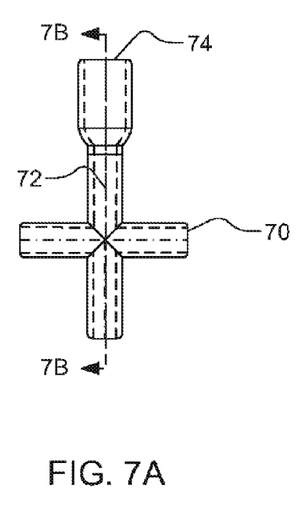
FIG. 7A is a side view of an embodiment of a connector.
Figure 7B:
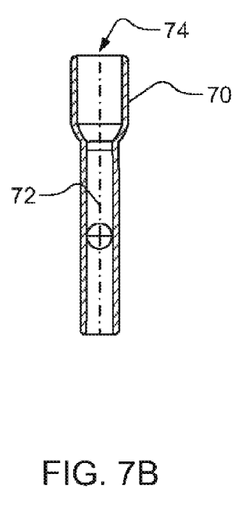
FIG. 7B is a cross-sectional view of the connector shown in FIG. 7A, taken along line 7B-7B.

As another example, FIGS. 7A and 7B show a cross-shaped connector 70 having a passageway 72 with a varying cross-sectional diameter or width. As shown, passageway 72 increases in diameter as it extends to end opening 74, for example, to attach to a larger sized conduit or connector. The change in diameter is smooth (e.g., without an abrupt step) to prevent material from accumulating in passageway 72. In other embodiments, a passageway decreases in diameter or width as it extends to an end opening. A connector can have multiple passageways that vary in cross-sectional diameter or width.

In some embodiments, the conduits, connectors and polymeric members can be fabricated with materials having different colors, e.g., according to the desired color code. The different colors can facilitate assembly and inspection of the fluid transfer assembly, and confirmation that the assembly has been correctly configured, for example.

While fluid transfer assembly 20 is shown having connectors attached to conduits, in other embodiments, one or more connectors can be directly attached to one or more other connectors.

Connectors having five or more (e.g., six, seven, eight, nine, ten or more) end openings can be formed; and/or connectors having four or more (e.g., five, six, seven, eight, nine, ten or more) passageways can be formed, according to fluid transfer assembly to be formed. The shape of a connector can be symmetrical or non-symmetrical.

Within a fluid transfer assembly, the connectors, conduits, and polymeric members can be the same or different, for example, in terms of size, chemical composition, shape, color, and configuration.

Figure 8:
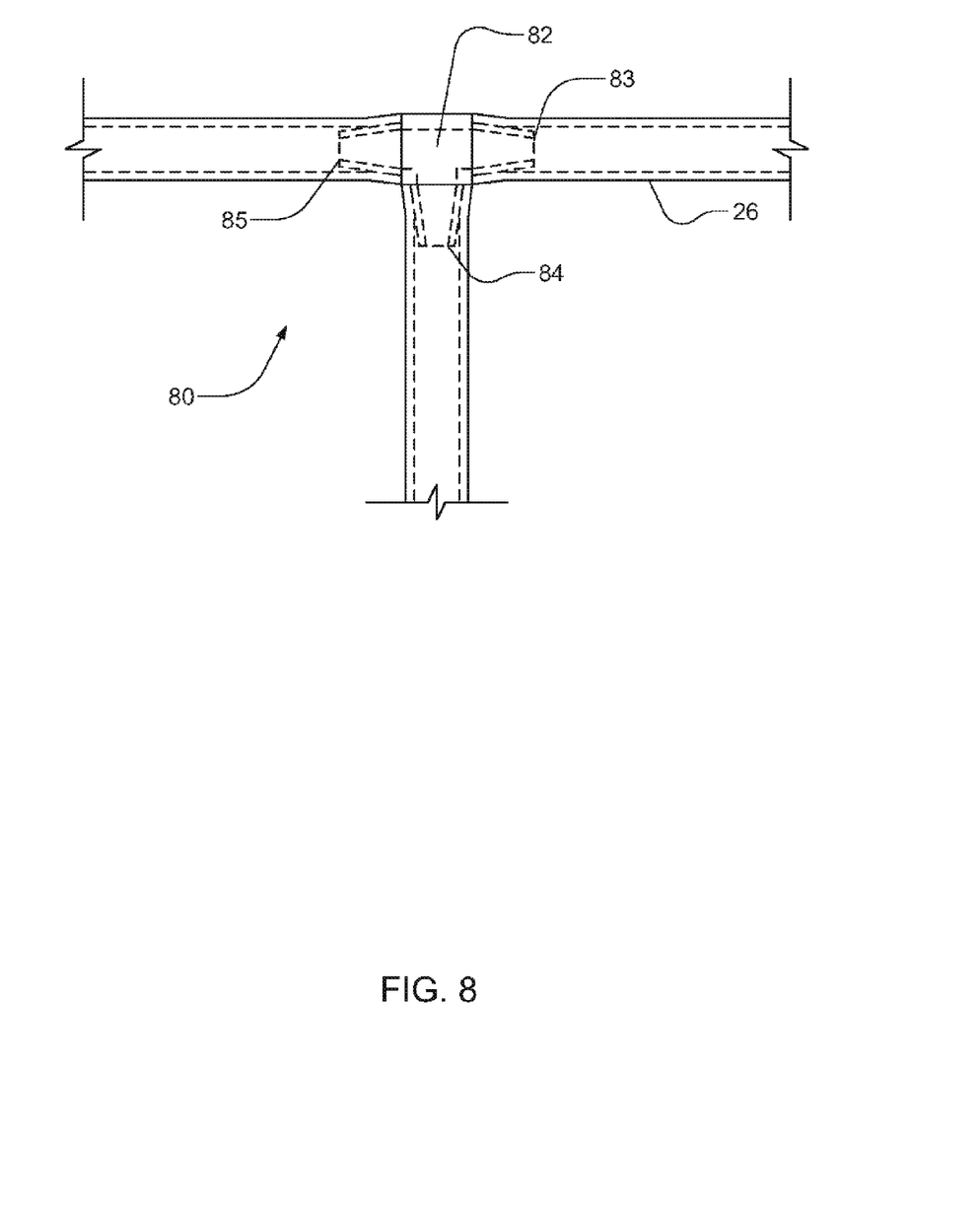
FIG. 8 is a side view of an embodiment of an assembly using an internal T connector.

Burst strength was tested using ASTM D-1599 "Standard Test Method for Resistance to Short-Time Hydraulic Pressure of Plastic Pipe, Tubing, and Fittings." Results for burst tests using ASTM D-1599 are provided for: a) C-FLEX conduit alone (10" tubes); b) C-FLEX conduit and connectors in an overmolded T configuration with filled gaps as shown in FIG. 2B (Assembly A); and c) an assembly 80 of C-FLEX connectors and conduit joined by a standard internal T connector as shown in FIG. 8 (Assembly B). Although not shown in FIG. 8, Assembly B was overmolded so that the entire assembly was encapsulated by a polymeric member beyond ends 83, 84 and 85 of internal T connector 82. Internal T connector 82 was of C-FLEX material having a Shore A hardness of 95. In both Assembly A and Assembly B the overmolded polymeric member was of C-FLEX, the same material from which the conduits and connectors were made. All testing was performed at 73° F.

Figure 9:
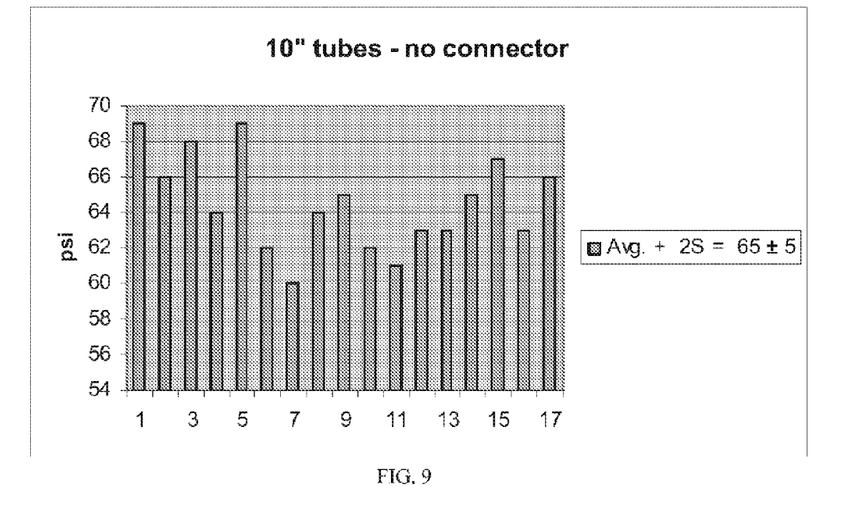
FIG. 9 is a bar graph showing burst test results for tubing alone.
Figure 10:
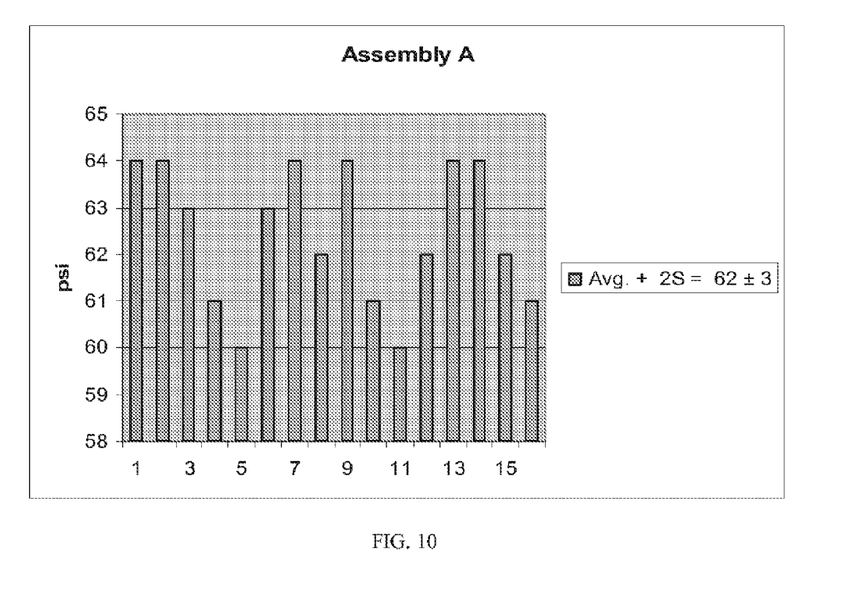
FIG. 10 is a bar graph showing burst test results for an embodiment of a connector connected to tubing.
Figure 11:
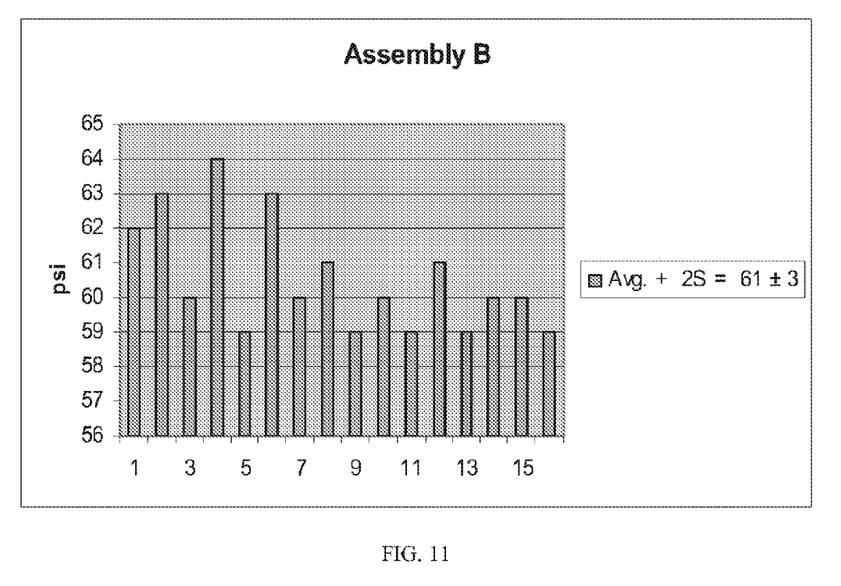
FIG. 11 is a bar graph showing burst test results for another embodiment of a connector connected to tubing.

Burst test results for the C-FLEX conduit alone are provided in graphical form in FIG. 9. Seventeen samples were tested resulting in an Average Burst Pressure of 65 psi. Results for Assembly A are provided graphically in FIG. 10 and show an Average Burst Pressure of 62 psi. Results for Assembly B are provided graphically in FIG. 11 and show an Average Burst Pressure of 61 psi. Thus both Assembly A and Assembly B indicated a burst test pressure within 10% of the conduit absent any connector at all. A first burst strength is considered to be substantially equivalent to a second burst strength if it is within 10% of the value of the second burst strength. Assembly A, which had no internal T joining the three conduits together, provided a higher burst test pressure than did Assembly B. Assembly A, unlike Assembly B, had no regions with an inner diameter less than that of the conduits and/or connectors.

Tensile strength was also evaluated for Assembly A and Assembly B. A modified version of ASTM D-412 was used in which opposed conduits on each assembly were gripped at a point 4 inches to either side of the connector and placed in a state of increasing tension until failure. The tension at which each sample failed was recorded. 24 samples of Assembly A and 25 samples of Assembly B were evaluated. Results for Assembly A show an average load at peak tension of 352 psi with a standard deviation of 16.7. Results for Assembly B show an average load at peak tension of 505.7 psi with a standard deviation of 27.0. Although the tension limits for Assembly A were below those for Assembly B, the values are still well above minimum limits for assemblies of this type.

As the tensile strength test was performed on tubing and connectors, an additional nine samples of Assembly A and nine samples of Assembly B were tested and the force (without regard to a specific area of the tubing) required for the assembly to fail was recorded. For Assembly A the average force at failure was 402.4 N with a standard deviation of 23.9. Eight of the Assembly A samples failed at the junction of the tube and the T connection while one failed in the middle of the T. For Assembly B, the average force at failure was 511.4 N with a standard deviation of 28.7. Four of these samples failed at the junction of the tubing and the connector, four failed at the tubing about 1 cm from the junction and one failed at the grip. Although Assembly A results were about 20% below those of Assembly B, the values were still well above threshold levels for fluid distribution systems of this type.

All references, such as patents, patent applications, and publications, referred to above are incorporated by reference in their entirety.

Other embodiments are within the scope of the following claims.

What is claimed is:

1. An assembly, comprising:
   a first polymeric connector having a first passageway aligned in a first direction and a second passageway aligned in a second direction, wherein the first direction is fixed relative to the second direction;
   a first flexible, polymeric conduit having a conduit passageway in fluid communication with the first passageway of the first polymeric connector, wherein the first flexible, polymeric conduit includes an elastomer, a thermoplastic elastomer, an engineering thermoplastic elastomer, or any combination thereof; and
   a first polymeric member extending into a gap defined between the first polymeric connector and the first polymeric conduit and extending over said gap and at least portions of outer surfaces of the first polymeric connector and the first polymeric conduit, wherein the first polymeric member, the first polymeric conduit and the first polymeric connector are aligned to provide a substantially smooth, seamless transition between an inner diameter of the first polymeric connector and an inner diameter of the first polymeric conduit.

2. The assembly of claim 1, wherein a portion of the first polymeric member extends over said gap and the portion of the polymeric member extending over the gap has a substantially content outer diameter.

3. The assembly of claim 1, wherein the first polymeric connector comprises three or more end openings.

4. The assembly of claim 1, further comprising a second polymeric conduit having a conduit passageway attached to the first polymeric connector with a second polymeric member extending over at least portions of outer surfaces of the first polymeric connector and the second polymeric conduit, the second passageway of the first polymeric connector being in fluid communication with the conduit passageway of the second polymeric conduit.

5. The assembly of claim 1, further comprising a second polymeric connector having a fourth passageway and a fifth passageway fixed relative to the fourth passageway attached to the first polymeric connector with a second polymeric member extending over at least portions of outer surfaces of the first polymeric connector and the second polymeric connector, the second passageway being in fluid communication with the fourth passageway.

6. The assembly of claim 1, wherein the first polymeric connector, the first polymeric conduit, and the first polymeric member comprise one or more thermoplastic elastomers.

7. The assembly of claim 1, wherein an inner diameter of a lumen of the polymeric member at the gap is substantially the same as the inner diameter of the first polymeric conduit and the first polymeric connector.

8. The assembly of claim 1, having a burst strength substantially equivalent to a burst strength of the first polymeric conduit.

9. The assembly of claim 1, wherein the first polymeric member contacts the first polymeric connector and the first polymeric conduit.

10. The assembly of claim 1, wherein the flexible, polymeric conduit is a flexible body having the first and the second passageways.

11. The assembly of claim 1, wherein the first polymeric connector includes a different composition than a composition of the first polymeric member.

12. A method of attaching a first polymeric connector having a first passageway aligned in a first direction and a second passageway aligned in a second direction and fixed relative to the first passageway, and a first flexible, polymeric conduit having a third passageway, the method comprising:
   attaching the first polymeric connector to the first flexible, polymeric conduit with a first polymeric member extending over at least portions of outer surfaces of the first connector and the first conduit, the first passageway being in fluid communication with the third passageway,
   wherein the first polymeric member extends into a gap defined between ends of the first polymeric connector and the first polymeric conduit, and wherein the first polymeric conduit includes an elastomer, a thermoplastic elastomer, an engineering thermoplastic elastomer, or any combination thereof and,
   wherein the first polymeric member, the first polymeric conduit and the first polymeric connector are aligned to provide a substantially smooth, seamless transition between an inner diameter of the first polymeric connector and an inner diameter of the first polymeric conduit.

13. The method of claim 12, wherein the first polymeric connector and the first polymeric conduit have inner widths or diameters that are substantially the same.

14. The method of claim 12, wherein at least portions of the first and third passageways are substantially flush.

15. The method of claim 12, wherein the first connector comprises three or more end openings.

16. The method of claim 12, comprising injection molding the first polymeric member.

17. The method of claim 16 wherein two or more polymeric members are molded simultaneously.

18. The method of claim 12, further comprising attaching a second polymeric conduit having a fourth passageway to the first polymeric connector with a second polymeric member extending over at least portions of outer surfaces of the first polymeric connector and the second polymeric conduit, the second passageway being in fluid communication with the fourth passageway.

19. The method of claim 12, further comprising attaching a second polymeric connector having a fourth passageway and a fifth passageway fixed relative to the fourth passageway to the first polymeric connector with a second polymeric member extending over at least portions of outer surfaces of the first polymeric connector and the second polymeric connector, the second passageway being in fluid communication with the fourth passageway.

20. The method of claim 12, wherein the first polymeric connector, the first polymeric conduit, and the first polymeric member comprise one or more thermoplastic elastomers.

* * * * *